United States Patent [19]

Hodges et al.

[11] Patent Number: 5,225,202
[45] Date of Patent: Jul. 6, 1993

[54] ENTERIC COATED PHARMACEUTICAL COMPOSITIONS

[75] Inventors: Garry R. Hodges; David L. McCann, both of Merseyside, England

[73] Assignee: E. R. Squibb & Sons, Inc., Princeton, N.J.

[21] Appl. No.: 767,967

[22] Filed: Sep. 30, 1991

[51] Int. Cl.⁵ .............................................. A61K 9/16
[52] U.S. Cl. ........................... 424/480; 424/486; 424/461; 424/462; 424/494; 424/497
[58] Field of Search ............... 424/459, 490, 480, 486, 424/461, 462, 494, 497; 546/206

[56] References Cited

U.S. PATENT DOCUMENTS

| | | | |
|---|---|---|---|
| 4,017,647 | 4/1977 | Ohno | 424/463 |
| 4,346,227 | 8/1982 | Terahara | 549/292 |
| 4,524,060 | 6/1985 | Mughal | 424/459 |
| 4,728,512 | 3/1988 | Mehta | 424/458 |
| 4,794,001 | 12/1988 | Mehta | 424/458 |
| 4,808,413 | 2/1989 | Joshi | 424/458 |
| 4,857,522 | 8/1989 | DiPietro | 546/206 |
| 4,994,279 | 2/1991 | Aoki | 424/490 |
| 5,026,559 | 6/1991 | Eichel | 424/490 |
| 5,026,560 | 6/1991 | Makino | 424/490 |

FOREIGN PATENT DOCUMENTS

| | | |
|---|---|---|
| 0375156 | 6/1990 | European Pat. Off. |
| 1483423 | 8/1977 | United Kingdom . |
| 2057876A | 4/1981 | United Kingdom . |

OTHER PUBLICATIONS

Stafford, J. W., Drug Dev. Ind. Pharm., 8(4), 513-530 (1982).
Bloor, J. R., et al., Drug Dev. Ind. Pharms., 15(14-16), 2227-2243 (1989).

Primary Examiner—Thurman K. Page
Assistant Examiner—William E. Benston
Attorney, Agent, or Firm—Burton Rodney

[57] ABSTRACT

An enteric coated pharmaceutical composition is provided which includes a medicament which is sensitive to a low pH environment of less than 3, such as pravastatin, which composition is preferably in the form of pellets which includes an enteric coating formed of neutralized hydroxypropylmethyl cellulose phthalate, plasticizer and anti-adherent. The so-coated pellets have good resistance to deterioration at pH less than 3 but have good drug release properties at greater than 3.

33 Claims, 1 Drawing Sheet

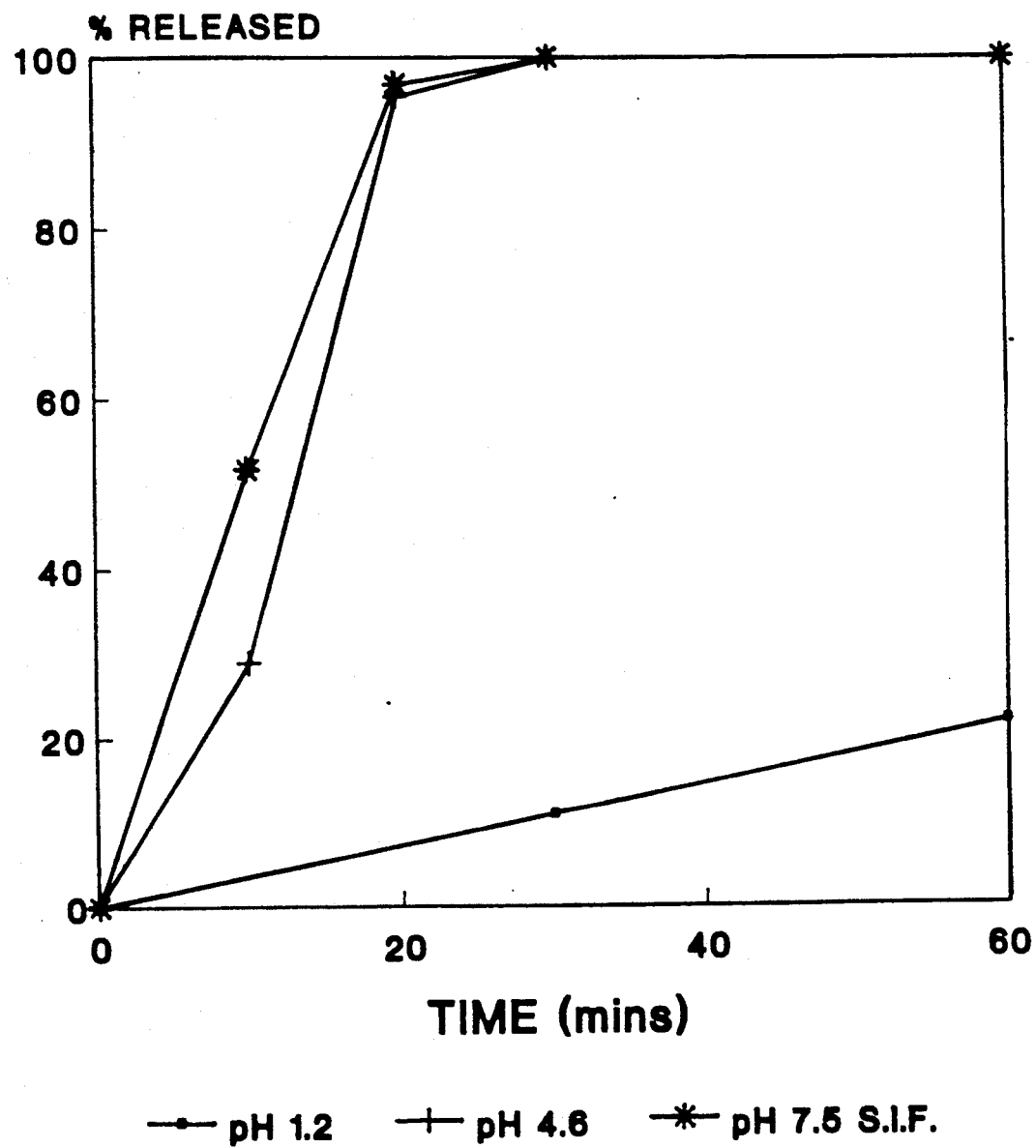

ENTERIC COATED PHARMACEUTICAL COMPOSITIONS

FIELD OF THE INVENTION

The present invention relates to an enteric coated pharmaceutical composition, preferably in the form of pellets, which includes a medicament which is sensitive to a low pH environment of less than 3, such as pravastatin, yet such composition has good protection (that is low rates of drug release) at such low pH, but has good drug release properties at pH's greater than 3.

BACKGROUND OF THE INVENTION

Enteric coatings have long been used to inhibit release of drug from tablets and pellets. The enteric coatings are resistant to stomach acid for required periods of time depending on the composition and/or thickness thereof, before they begin to disintegrate and allow for slow release of drug in the stomach and/or upper intestines. Some examples of coatings previously employed are beeswax and glyceryl monostearate; beeswax, shellac and cellulose; and cetyl alcohol, mastic and shellac as well as shellac and stearic acid (U.S. Pat. No. 2,809,918); polyvinylacetate and ethyl cellulose (U.S. Pat. No. 3,835,221); and neutral copolymer of polymethacrylic acid esters (Eudragit L30D). (F. W. Goodhart et al, Pharm. Tech., pp 64–71, April, 1984); copolymers of methacrylic acid and methacrylic acid methyl ester (Eudragits), or a neutral copolymer of polymethacrylic acid esters containing metallic stearates (Mehta et al U.S. Pat. Nos. 4,728,512 and 4,794,001).

Most available enteric coating polymers begin to become soluble at pH 5.5 and above, with maximum solubility rates at pH's greater than 6.5.

Hydroxypropylmethyl cellulose phthalate (HPMCP) is available from Shin-Etsu Chemical Co., Ltd. who recommend application of this polymer, for use in enteric coatings, in its natural acidic form from organic solvents. This material starts its dissolution process at pH 5.0.

Stafford, J. W., Drug Dev. Ind. Pharm., 8(4), 513–530 (1982) and Bloor, J. R. et al, Drug Dev. Ind. Pharm., 15(14–16), 2227–2243 (1989) describe the use of HPMCP as its totally neutralized form (treated with sodium hydroxide) as an enteric coating applied from aqueous systems. Aqueous systems are preferred due to environmental concerns and flammability/explosion concerns with solvents.

U.S. Pat. No. 4,017,647 and British Patent Specification 1,483,423 discloses HPMCP dissolved in water by neutralizing with a base and applied to tablets or granules by a spray coating technique. However, the coatings are not enteric until they undergo a subsequent acid treatment.

U.K. Patent Application GB 2,057,876A discloses use of HPMCP as its totally neutralized form (treated with sodium hydroxide or ammonium hydroxide) as an enteric coating applied from aqueous systems which coating remains intact for at least 1 hour in contact with HCl of pH 1.2 at 36° to 38° C. and disintegrates within 60 minutes when the pH is raised to 6.8, for example, in a KH$_2$PO$_4$ buffered solution.

Unfortunately, where it has been attempted to coat pellets using a film coating formulation designed for coating tablets, but including a totally neutralized form of HPMCP, as described in the above references, it has been found that unsatisfactory processing results are obtained due to mass differences between tablets and pellets. The tablet film coating formulation causes significant adherence and clumping of the pellets.

Pharmaceutical compositions which include a medicament which is unstable in an acidic environment such as the stomach will require an enteric protective coating to prevent release of such medicament prior to reaching the intestines.

Pravastatin, an HMG CoA reductase inhibitor disclosed in Terahara et al U.S. Pat. No. 4,346,227 and having the formula

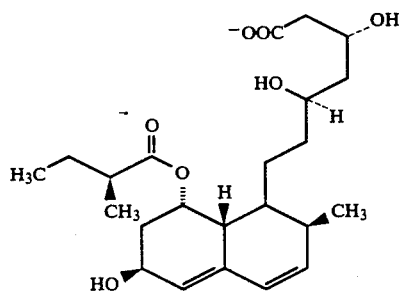

is sensitive to a low pH environment and will degrade in the stomach.

BRIEF DESCRIPTION OF THE DRAWING

The accompanying figure is A graph of % release of pravastatin (from enteric coated pellets in accordance with the invention) vs. time at ph 1.2, 4.6 and 7.5.

DESCRIPTION OF THE INVENTION

In accordance with the present invention, an enteric coated pharmaceutical composition is provided which includes a medicament which may degrade in a low pH environment but which is protected by the enteric coating from doing so. The pharmaceutical composition of the invention, which is preferably in the form of a pellet or small tablet, includes a core which includes a medicament which is sensitive to a low pH environment, such as pravastatin, a disintegrant or swelling agent, and a buffering agent, and an enteric coating surrounding the core which coating will include a neutralized form of hydroxypropylmethyl cellulose phthalate, and plasticizer(s) and anti-adherent (in the case of coating of pellets).

The novel enteric coated pharmaceutical of the invention will provide for protection of the medicament, such as pravastatin, at pH's less than 3 (such as found in the stomach) but will allow for rapid drug release at a pH of 4.5 or higher (such as found in the upper intestines) that is at least one pH unit lower than previously thought possible for coating material containing neutralized HPMCP.

Accordingly, the pharmaceutical composition of the invention will usually include drugs which are chemically unstable in acidic environments but which also have narrow "absorption windows" high up in the GI tract. The pharmaceutical composition of the invention gives good protection in very acidic environments (pH <3) whilst not delaying the rapid release in regions of good drug absorption (pH >4), whether this be the upper intestine or the stomach.

The core of the pharmaceutical composition of the invention will include one or more fillers, such as lactose and/or microcrystalline cellulose, one or more binders, such as polyvinylpyrrolidone, one or more disintegrating agents such as croscarmellose sodium, one or more buffering agents such as sodium acetate or sodium citrate, and optionally one or more lubricants such as magnesium stearate.

The buffering agent will be included to ensure rapid drug release between pH's 4 and 5 and to aid in minimizing drug degradation in the core due to acid ingress in low pH environments.

The invention is particularly adapted to pharmaceutical compositions such as pellets or tablets, preferably pellets, containing pravastatin as the medicament. Pravastatin, will be present in an amount within the range of from about 1 to about 60% and preferably from about 3 to about 50% by weight of the composition.

The pharmaceutical present in the core will be an acid labile drug such as pravastatin, erythromycin, ddI (dideoxyinosine), digoxin, pancreatin, ddA, ddC, and the like.

The core of the composition of the invention will include one or more disintergrants or swelling agents in an amount within the range of from about 1 to about 20% and preferably from about 2 to about 15% by weight of the composition such as croscarmellose sodium, sodium starch glycolate, corn starch, or cross-linked polyvinylpyrollidone.

When the core is a tablet it may optionally include tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like.

The buffering agent will be present in the core in an amount within the range of from about 1 to about 20% by weight and preferably from about 2 to about 15% by weight of the composition. Examples of buffering agents which may be included herein include but are not limited to sodium acetate, sodium citrate, sodium tartrate, sodium fumarate, sodium malate, sodium succinate, magnesium oxide, aluminum oxide, dihydroxy aluminum sodium carbonate, an alkaline earth metal hydroxide such as calcium hydroxide or magnesium hydroxide, with sodium acetate or sodium citrate being preferred.

The core of the composition of the invention will also preferably include one or more fillers or excipients in an amount within the range of from about 5 to about 90% by weight and preferably from about 10 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders will preferably be present in the core, in addition to or in lieu of the fillers, in an amount within the range of from 0 to about 20% and preferably from about 2 to about 15% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Other conventional ingredients which may optionally be present in the core include preservatives, stabilizers, anti-adherents or silica flow conditioners or glidants, such as Syloid brand silicon dioxide as well as FD&C colors.

In forming the enteric coated pharmaceutical composition of the invention, an enteric coating solution will be employed which will contain neutralized HPMCP that is hydroxypropylmethyl cellulose phthalate neutralized with sodium hydroxide or other base as disclosed in U.S. Pat. No. 4,017,647 and in the Stafford, supra and Bloor et al, supra, papers discussed hereinbefore.

The term "neutralized HPMCP" or "neutralized hydroxypropylmethyl cellulose phthalate" as employed herein refers to hydroxypropylmethyl cellulose phthalate which has been totally neutralized or preferably partially neutralized, that is from about 80 to about 95% neutralized.

The enteric coating will also preferably contain a plasticizer such as triethyl citrate (Citroflex 2), diethylphthalate, triacetin, tributyl sebacate, or polyethylene glycol, preferably Citroflex 2, preferably an antiadherent (where the coating is to be applied to a pellet) such as talc, fumed silica or magnesium stearate, with talc being preferred, all of which is carried in aqueous medium. The aqueous medium will be in an amount sufficient to disperse all of the above materials.

The enteric coating solution employed is substantially easier to process than previously reported coating systems, and can be used to coat small diameter, low mass particles (pellets) using a continuous coating run with minimal processing problems (agglomeration), without the need for organic solvents.

The above enteric coating solution will include the HPMCP (preferably of the type HP-50F, Shin-Etsu Chemical Co., Ltd. containing from about 21 to 27% phthalyl content) in an amount within the range of from about 40 to about 75% by weight and preferably from about 45 to about 70% by weight based on solids content of the enteric coating solution, HPMCP neutralizing agent such as sodium hydroxide, potassium hydroxide or ammonia, preferably sodium hydroxide, in an amount within the range of from about 1.5 to about 5% by weight and preferably from about 2 to about 4% by weight, plasticizer in an amount within the range of from about 12 to about 30% by weight and preferably from about 15 to about 25% by weight, where the core to be coated is a pellet, anti-adherent in an amount within the range of from about 15 to about 35% by weight and preferably from about 20 to about 30% by weight, and optionally an antifoam emulsion such as a silicon emulsion, in an amount within the range of from about 0 to about 3% by weight.

All of the above weights are based on total concentration of the solids or non-aqueous components of the enteric coating solution.

The enteric coating solution will thus contain from about 5 to about 20% by weight solids or nonaqueous component, and from about 80 to about 95% by weight water.

Where the core includes a drug which is incompatible with the enteric coating layer, a subcoat layer which acts as a physical barrier between the core and outer enteric coating layer will be employed. Inasmuch as the subcoat layer is non-functional as far as dissolution performance is concerned, any compatible non-functional film former can be employed.

For example, the subcoat layer will include one or more film-formers or binders, such as a non-ionic hydrophilic polymer like hydroxypropylmethyl cellulose and a plasticizer such as polyethylene glycol, triethyl citrate, diethyl phthalate, propylene glycol, glycerin, butyl phthlate, castor oil and the like.

The subcoat layer may be applied by conventional coating techniques, preferably employing aqueous systems.

The enteric coating will be present in a weight ratio to the core of within the range of from about 0.2:1 to about 0.4:1.

Where present, the subcoat layer will be employed in a weight ratio to the enteric coating layer of within the range of from about 0.05:1 to about 0.2:1.

The core employed in the pharmaceutical composition of the invention may be formed of a pellet or beadlet or tablet, preferably having a diameter of from about 0.8 to about 6 mm, preferably from about 1 to about 3 mm. The core will preferably comprise a pellet or beadlet.

A preferred enteric coated pellet formulation is set out below.

| Material | Possible Range % | Preferred Range % |
| --- | --- | --- |
| CORE | | |
| Drug (Pravastatin Sodium) | 1–60 | 5–40 |
| Microcrystalline Cellulose (Avicel PH101) | 10–60 | 15–50 |
| Lactose | 10–70 | 10–60 |
| Sodium Starch Glycollate | 1–20 | 2–15 |
| Sodium Citrate | 1–20 | 2–10 |
| Polyvinylpyrollidone | 0–20 | 2–15 |
| SUBCOAT | | |
| Pharmacoat 603 (HPMC) | 60–95 | 75–90 |
| Polyethylene Glycol 400 | 5–40 | 10–25 |
| OVERCOAT | | |
| HPMCP HP-50F | 40–75 | 45–70 |
| Citroflex 2 | 12–30 | 15–25 |
| Sodium Hydroxide | 2–4 | 2–4 |
| Talc | 15–35 | 20–30 |
| Antifoam Emulsion | 0–3 | 0–3 |

Th enteric coated pharmaceutical composition in the form of pellets or beadlets may be prepared employing an extrusion-spheronization procedure such as described in Joshi et al U.S. Pat. No. 4,808,413. For example, the pharmaceutical (preferably pravastatin) is dissolved in a granulation liquid (water). The fillers, binders, disintegrants and buffering agent (for example, microcrystalline cellulose, lactose, sodium starch glycollate, polyvinylpyrollidone and sodium citrate) are thoroughly mixed, for example, using a conventional mixer such as a planetary mixer, to form a dry blend. The dry blend is then granulated using the above granulation solution and continued to the endpoint with water. The wet mass is extruded, for example, employing a Nica, Luwa or other type extruder to form an extrudate which is then passed through spheronizing equipment, such as Nica, Luwa or other type, which converts the extrudate into beadlets of appropriate particle size range. The beadlets may then be dried by tray drying oven or fluid bed drying. Where the core is to be a tablet, the tablet may be formed using conventional techniques.

The dried beadlets or pellets, or tablets may then be coated with a subcoat, for example, with a solution of hydroxypropylmethyl cellulose (Pharmacoat 603) and polyethylene glycol 400. These sub-coated beadlets or pellets are then overcoated with an enteric coating composition such as a dispersion of HPMCP neutralized with sodium hydroxide, Citroflex 2, talc and silicon emulsion.

The so-formed pellets, beadlets or tablets may be filled into hard shell capsules.

The accompanying Figure is a graph of % release of pravastatin (from enteric coated pellets in accordance with the invention) vs. time at various pHs.

The following Examples represent preferred embodiments of the present invention. All temperatures are expressed in degree Centigrade unless otherwise indicated and all mesh sizes are U.S. Standard STME.

EXAMPLE 1

A pravastatin formulation in the form of enteric coated pellets having the following composition was prepared as described below.

| COMPOSITION | WEIGHT % OF COMPONENT | WEIGHT % OF FINAL FORMULATION |
| --- | --- | --- |
| A: PELLET CORE | | |
| Pravastatin Sodium | 12.0) | *8.36–8.87 |
| Avicel PH101 (microcrystalline cellulose) | 21.0) | 14.63–15.53 |
| Lactose BP | 50.0) | 34.82–36.97 |
| Sodium Starch Glycolate | 10.0) | 6.97–7.39 |
| Sodium Citrate | 5.0) | 3.48–3.70 |
| Polyvinylpyrollidone | 2.0) | 1.39–1.48 |
| B: SUBCOAT | | |
| Pharmacoat 603 (HPMC) | 90.0) | 1.88–2.00 |
| Polyethylene glycol 400 | 10.0) | 0.21–0.22 |
| C: OVERCOAT | | |
| HPMCP HP-50 F | 51.19–50.82)* | 12.21–14.36 |
| Citroflex 2 | 20.48–20.33) | 4.88–5.74 |
| Sodium Hydroxide | 2.60–3.31) | 0.62–0.94 |
| Talc | 25.60–25 41) | 6.10–7.18 |
| Antifoam Emulsion M30 (silicon emulsion) | 0.13–0.13) | 0.03–0.04 |
| D: CAPSULE | | |
| Size 0 clear body and cap | | |

*range dependent upon phthalyl content of HPMCP HP-50F (21–27%)

Pravastatin sodium was dissolved in water which serves as granulation fluid. Microcrystalline cellulose, sodium starch glycollate, polyvinylpyrollidone, lactose and sodium citrate were dry blended in a planetary mixer.

The dry blend was then granulated using the pravastatin sodium solution and continued to the endpoint with water. The wet mass was extruded and spheronized and then oven dried to a moisture content of less than 3%.

The dried pellets were then coated with a solution of HPMC and polyethylene glycol 400. The sub-coated pellets were then overcoated with a 90% neutralized HPMCP, Citroflex 2, talc and silicon emulsion.

The enteric coated pravastatin pellets were then filled into capsules (clear body and cap, size 0).

The so formed pravastatin enteric coated product was found to have good protection against gastric acid (at pH of 1.2) but had good release rate of pravastatin at pH's between 4 and 5 and at pH 7.5.

EXAMPLE 2

A preferred pravastatin formulation in the form of enteric coated pellets was prepared as described below.

Pravastatin sodium (840 g) was dissolved in water (1785 g) which serves as the granulation fluid. Microcrystalline cellulose (1470 g), sodium starch glycolate (700 g), polyvinylpyrollidone (140 g), lactose (3500 g) and sodium citrate (350 g) were dry blended in a planetary mixer The dry blend was then granulated using the pravastatin sodium solution (2625 g) and continued to the endpoint with water. The wet mass was extruded through a 1.2 mm screen using a Nica extruder and spheronised for 2 minutes at 600 rpm using a Caleva spheroniser. The pellets were oven dried to a moisture content of less than 3%.

The dried pellets (2 kg) were loaded into the column of an Aeromatic MP1 fluidised bed apparatus. The pellets were subcoated with 600 g of the solution given below:

| | |
|---|---|
| Pharmacoat 603 (HPMC) | 54 g |
| Polyethylene glycol 400 | 6 g |
| Water | 540 g |
| using the following conditions: | |
| Spray gun nozzle aperture | 0.8 mm |
| Atomising air pressure | 1.8-2.0 bar |
| Coating solution flow rate (initial) | 3.5 gmin$^{-1}$kg$^{-1}$ |
| Inlet air temperature | 50° C. |
| Outlet air temperature | 32-38° C. |

The subcoated pellets were then overcoated with 5000 g of the solution given below:

| | |
|---|---|
| HPMCP (HP-50F) | 400 g |
| Triethylcitrate | 160 g |
| Sodium hydroxide | 21 g |
| Talc | 200 g |
| Antifoam emulsion | 1 g |
| Water | 4218 g |
| using the following conditions: | |
| Spray gun nozzle aperture | 0.8 mm |
| Atomizing air pressure | 1.8-2.0 Bar |
| Solution flow rate (initial) | 5 gmin$^{-1}$kg$^{-1}$ |
| Inlet air temperature | 50° C. |
| Outlet air temperature | 30-38° C. |

The coated pravastatin pellets were then filled into capsules.

The accompanying Figure shows % pravastatin released from the Example 2 enteric-coated formulation versus time at pH 1.2, pH 4.6 and pH 7.5.

The so-formed pravastatin enteric coated product was found to have good protection against gastric acid (at pH's of 1.2), but had good release rate of pravastatin at pH 4.6 and excellent release profile at pH 7.5.

What is claimed is:

1. An enteric coated pharmaceutical composition comprising a core in the form of a tablet, beadlet, pellet or particle and an enteric coating for said core, said core comprising an acid labile medicament in an amount within the range of from about 1 to about 60% by weight of the composition, a disintegrant in an amount within the range of from about 1 to about 20% by weight of the composition and a buffering agent in an amount within the range of from about 1 to about 20% by weight of the composition, and said enteric coating comprising a hydroxypropylmethyl cellulose phthalate which is totally neutralized or at least about 80% neutralized, and a plasticizer, said enteric coating imparting protection to said core so that said core is afforded protection in a low pH environment of 3 or less while capable of releasing medicament at a pH of 4.5 or higher.

2. The pharmaceutical composition as defined in claim 1 wherein the enteric coating includes an anti-adherent in an amount within the range of from about 15 to about 35% by weight, and the core is in the form of a pellet.

3. The pharmaceutical composition as defined in claim 1 wherein the hydroxypropylmethyl cellulose phthalate is from about 80 to about 95% neutralized.

4. The pharmaceutical composition as defined in claim 3 wherein the hydroxypropylmethyl cellulose phthalate is neutralized with an alkali metal hydroxide employed in an amount within the range of from about 1.5 to about 5% by weight of the enteric coating.

5. The pharmaceutical composition as defined in claim 4 wherein the alkali metal hydroxide is sodium hydroxide.

6. The pharmaceutical composition as defined in claim 1 wherein the plasticizer is triethyl citrate, diethyl phthalate, triacetin or polyethylene glycol, and is present in an amount within the range of from about 12 to about 30% by weight of the enteric coating.

7. The pharmaceutical composition as defined in claim 1 wherein the plasticizer is triethyl citrate.

8. The pharmaceutical composition as defined in claim 2 wherein the anti-adherent is fumed silica, magnesium stearate or talc.

9. The pharmaceutical composition as defined in claim 8 wherein the anti-adherent is talc.

10. The pharmaceutical composition as defined in claim 2 wherein the enteric coating is present in a weight ratio to the core of within the range of from about 0.2:1 to about 0.4:1.

11. The pharmaceutical composition as defined in claim 2 wherein the enteric coating includes the hydroxypropylmethyl cellulose phthalate in an amount within the range of from about 40 to about 75% by weight, the plasticizer is present in an amount within the range of from about 12 to about 30% by weight, and the anti-adherent is present in an amount within the range of from about 15 to about 35% by weight, all of the above % being based on the solids content of the enteric coating.

12. The pharmaceutical composition as defined in claim 11 wherein said enteric coating further includes an antifoam agent.

13. The pharmaceutical composition as defined in claim 11 wherein the enteric coating includes hydroxypropylmethyl cellulose phthalate, sodium hydroxide, Citroflex 2, talc and silicon emulsion.

14. The pharmaceutical composition as defined in claim 1 wherein said medicament is present in an amount within the range of from about 3 to about 50% by weight of the composition.

15. The pharmaceutical composition as defined in claim 1 wherein the medicament is pravastatin.

16. The pharmaceutical composition as defined in claim 1 wherein the medicament is erythromycin, ddI, digoxin, pancreatin, ddA or ddC.

17. The pharmaceutical composition as defined in claim 1 wherein the core includes disintegrant present in an amount within the range of from about 2 to about 15% by weight.

18. The pharmaceutical composition as defined in claim 17 wherein the disintegrant is croscarmellose sodium, crospovidone, sodium starch glycolate, or corn starch.

19. The pharmaceutical composition as defined in claim 1 wherein the core includes a buffering agent present in an amount within the range of from about 2 to about 15% by weight of the composition.

20. The pharmaceutical composition as defined in claim 19 wherein the buffering agent is sodium acetate, sodium citrate, sodium tartrate, dihydroxy aluminum sodium carbonate, sodium malate, sodium succinate, magnesium oxide, aluminum oxide or an alkaline earth metal hydroxide.

21. The pharmaceutical composition as defined in claim 20 wherein the buffering agent is sodium acetate or sodium citrate.

22. The pharmaceutical composition as defined in claim 1 wherein the core includes filler present in an amount within the range of from about 5 to about 90% by weight.

23. The pharmaceutical composition as defined in claim 22 wherein the filler is lactose, sugar, corn starch, modified corn starch, mannitol, sorbitol, wood cellulose, microcrystalline cellulose, calcium carbonate or mixtures thereof.

24. The pharmaceutical composition as defined in claim 1 wherein the core includes binder present in an amount within the range of from 0 to about 20% by weight.

25. The pharmaceutical composition as defined in claim 21 wherein the binder is microcrystalline cellulose, polyvinylpyrrollidone, lactose, corn starch, modified corn starch, sugars, gum acacia, carnauba wax, paraffin, spermaceti, polyethylenes or microcrystalline wax.

26. The pharmaceutical composition as defined in claim 1 in the form of a pellet or beadlet, or tablet.

27. The pharmaceutical composition as defined in claim 26 in the form of a pellet or beadlet.

28. The pharmaceutical composition as defined in claim 1 further including a subcoat between said core and said enteric coating.

29. The pharmaceutical composition as defined in claim 1 wherein the subcoat is formed of hydroxypropylmethyl cellulose and polyethylene glycol.

30. The pharmaceutical composition as defined in claim 28 having the following composition:

| Material | % |
| --- | --- |
| CORE | |
| Pravastatin Sodium | 5-50 |
| Microcrystalline Cellulose (Avicel PH101) | 10-60 |
| Lactose | 10-70 |
| Sodium Starch Glycollate | 1-20 |
| Sodium Citrate | 1-20 |
| Polyvinylpyrrollidone | 0-15 |
| SUBCOAT | |
| Pharmacoat 603 (HPMC) | 60-95 |
| Polyethylene Glycol 400 | 5-40 |
| OVERCOAT | |
| HPMCP HP-50F | 40-70 |
| Citroflex 2 | 12-30 |
| Sodium Hydroxide | 2-4 |
| Talc | 20-30 |
| Antifoam Emulsion | 0-3 |

31. An enteric coated pravastatin comprising a core in the form of a pellet, beadlet or tablet which includes pravastatin in an amount within the range of from about 1 to about 60% by weight and an enteric coating which includes a neutralized form of hydroxypropylmethyl cellulose phthalate which is totally neutralized or at least about 80% neutralized.

32. Pravastatin as defined in claim 31 in the form of pellets.

33. Pravastatin as defined in claim 32 wherein the enteric coating includes a neutralized form of hydroxypropylmethyl cellulose phthalate, a plasticizer and an anti-adherent.

* * * * *